United States Patent
Lopez

(10) Patent No.: US 6,809,671 B1
(45) Date of Patent: Oct. 26, 2004

(54) DYNAMIC GAIN CONTROL IN A DIGITAL EDDY CURRENT SIGNAL PROCESSOR

(75) Inventor: Estell Lopez, Issaquah, WA (US)

(73) Assignee: Zetec, Inc., Issaquah, WA (US)

(*) Notice: Subject to any disclaimer, the term of this patent is extended or adjusted under 35 U.S.C. 154(b) by 0 days.

(21) Appl. No.: 10/809,964

(22) Filed: Mar. 26, 2004

Related U.S. Application Data

(62) Division of application No. 10/266,845, filed on Oct. 8, 2002.

(51) Int. Cl.[7] .................................................. H03M 1/62
(52) U.S. Cl. ........................................ 341/139; 324/234
(58) Field of Search ............................. 324/234, 228, 324/226; 341/139

(56) References Cited

U.S. PATENT DOCUMENTS

| | | | | |
|---|---|---|---|---|
| 4,849,693 A | * | 7/1989 | Prince et al. ................ | 324/225 |
| 5,508,610 A | * | 4/1996 | Feeney et al. .............. | 324/233 |
| 6,734,669 B2 | * | 5/2004 | Lopez ........................ | 324/238 |

* cited by examiner

Primary Examiner—Brian Young
Assistant Examiner—Joseph Lauture
(74) Attorney, Agent, or Firm—David L. Tingey

(57) ABSTRACT

A digital synthesizer generates an electrical digital carrier that is converted to analog and driven a probe coil to generate an electromagnetic wave propagated into a test material proximate the probe coil. A return electromagnetic wave generated by eddy currents in the material includes signatures of material defects modulated on the return carrier electromagnetic wave. The return wave is detected by one or more probe coils and amplified. A second amplifier is applied selectively amplifying the signal in segments such that each segment exploits the input range of the analog to digital converter. The signal is then converted from an analog signal to a digital signal and then digitally mixed with digital sine and cosine functions also generated by the digital synthesizer to yield sum and difference values. A gain scaling stage then trims the signal to overcome circuit imprecision such that the amplification in each respective segment is a power of two. A low pass filter then removes all but the difference values, leaving only the small eddy current signal. A direct current reference component is subtracted from the mixed digital signal, which translates the signal to center about a zero axis for ease of display and analysis. A bit shifter than reverses the selective signal amplification by simply shifting bits in the digital representation of the signal corresponding to the prior selective amplification.

3 Claims, 5 Drawing Sheets

DYNAMIC GAIN CONTROL IN A DIGITAL EDDY CURRENT SIGNAL PROCESSOR

This is a divisional application of that application filed Oct. 8, 2002 under Ser. No. 10/266,845, which is still pending.

BACKGROUND

1. Field of Technology

This invention relates to eddy current signal processing, and more particularly to digital extraction of an eddy current signal employing dynamic signal amplification and phase compensation.

2. Prior Art

When an eddy current probe is in the vicinity of a flaw in a material, such as a hole or a crack, the flaw will modulate a carrier signal introduced into the material from an alternating current in a coil in the eddy current probe.

It is known to extract the signal through digital signal processing. Generally, a digital oscillator generates a digital carrier signal and corresponding sine and cosine waves. The carrier is then converted to an analog signal, low-pass filtered, and then directed to a probe coil that generates an electromagnetic field that penetrates into a nearby material. An eddy current is generated in the material, which generates its own electromagnetic field that is detected by the probe coil. When the material is without flaws, the two electromagnetic fields are largely out of phase and the fields partially cancel. However, when a flaw exists in the material, the amplitude and phase of the second field are modified and a small detectable signal results, modulated on the return carrier signal. A programmable return signal amplifier optimizes the input range of the analog to digital converter where the signal is converted to a digital signal. The signal is then mixed, or multiplied, with the digital sine and cosine waves. The signals out of the multipliers contain sum and difference products of the mixed signals that contain the amplitude and phase information of the material flaw. Low-pass filters then apply to reject all but the difference frequencies. Then a direct current signal is subtracted from the eddy current signal to shift its axis to zero, which makes it easier to display on a screen.

As stated, the return signal amplifier is to optimize the input range of the analog to digital converter. In doing so, it is limited to scaling the maximum amplitude to the input range of the converter. Though this is an advantage in expanding the eddy current signal modulated on the carrier signal, the small eddy current signal in parts of the return signal other than near the signal maximum amplitude remains relatively small, possibly with insufficient resolution to exploit the information it contains or buried in signal noise below the quantization noise of the analog to digital converter.

SUMMARY

A digital synthesizer generates an electrical digital carrier that is converted to an analog signal and then driven to a probe coil. The coil generates an electromagnetic wave that propagates into a test material proximate the probe coil. A return electromagnetic wave generated by eddy currents in the material includes signatures of material defects modulated on the return carrier electromagnetic wave. The return wave is detected by one or more probe coils and amplified by a return signal amplifier. The signal is then again selectively amplified. That is, sections of the signal out of the return signal amplifier with relatively small amplitudes are again amplified to also exploit the range of the analog to digital converter. Sections of the signal with relatively large amplitudes are less amplified or passed through unchanged. The result is a signal that more fully exploits the range of the analog to digital converter throughout the signal, not just at the signal maximum amplitude. This more general amplification then amplifies the carrier signal and the eddy current signal on the carrier signal even at low signal amplitudes to effectively present the carrier signal and the eddy current signal for digitization with improved signal resolution.

When the signal is demodulated by mixing with the digital sine and cosine functions and low pass filter, only the eddy current signal remains. However, the resultant eddy current signal with the selective amplification yields a high resolution representation of the eddy current signal and signature of the material defect.

To make the selective amplification transparent to the signal analyst, the signal must be restored, while carrying the improved resolution of the defect signature. A bit shifter is used to attenuate the digital output signals by the same ratio that the selectable amplifier amplifies the signal prior to the analog to digital converter. This is achieved by recording the performance of the selective amplifier in a reference memory and reversing it after demodulation of the signal by effecting the bit shift. The digital signal is represented in a series of words having a word width in bits more than needed to fully express the signal amplitude. When the digital signal is bit shifted, it simply moves into previously unused bit places.

The bit shifter operates as a power of two multiplier when shifted to the left into unused bits and a divider when shifted to the right. Therefore, to consistently match the bit shifter, the selectable amplifier must generally also employ quantized steps of amplification in powers of two.

If the gain of the selectable amplifier were constant across the frequency range, then nothing else would need to be added to the digital eddy current signal processor. However, as is the case with any analog amplifier, the magnitude and phase of the selectable amplifier change with respect to frequency. Furthermore, the requirement for amplification in steps of powers of two is ideal. The actual ratio of amplification obtained in a real circuit does not exactly equal a power of two because the tolerance of the resistors in the circuit will cause the ratio to vary slightly. Also, the parasitic capacitance of the circuit board will cause the phase of the selectable amplifier to vary. Therefore in order to accomplish the goal of transparent gain switching, the gain and phase changes of the selectable amplifier must be compensated.

A phase offset is added to the digital synthesizer of the carrier wave to compensate for the phase change of the selectable amplifier. The phase-offset value is equal but opposite to the phase change of the selectable amplifier at the frequency generated by the phase accumulator. The phase change will vary with the gain setting of the selectable amplifier, therefore the phase-offset value will vary to correspond to the gain setting. The phase-offset value, calculated in a calibration procedure, may be zero when the gain setting is low and equal but opposite to the phase change of the selectable amplifier when the gain setting is high.

The gain variation of the selectable amplifier is compensated with a scaling stage after the demodulating mixers but before the low pass filters. The gain-scaling value that is used in the scaling stage is also calculated in the calibration procedure.

BRIEF DESCRIPTION OF THE DRAWINGS

FIG. 2 shows in the first half of the figure a sinusoid carrier signal with amplitude equal to 1.0, representative of a small signal after the differential amplifier. The second half shows it with amplitude 4.0 after being amplified in the selective amplifier. If the signal size from the differential amplifier later increases, then the selectable amplifier may be returned to a gain of 1.0. In cases where the carrier is well rejected and the eddy current signal is large, the signal may rise above and fall below a threshold at which the gain of the selectable amplifier is switched. In this case, the reate at which the selectable gain is switched is fully dependent upon the frequency characteristics of the eddy current signal and it is independent of the carrier signal frequency.

DETAILED DESCRIPTION OF THE PREFERRED EMBODIMENT

Figure 1:
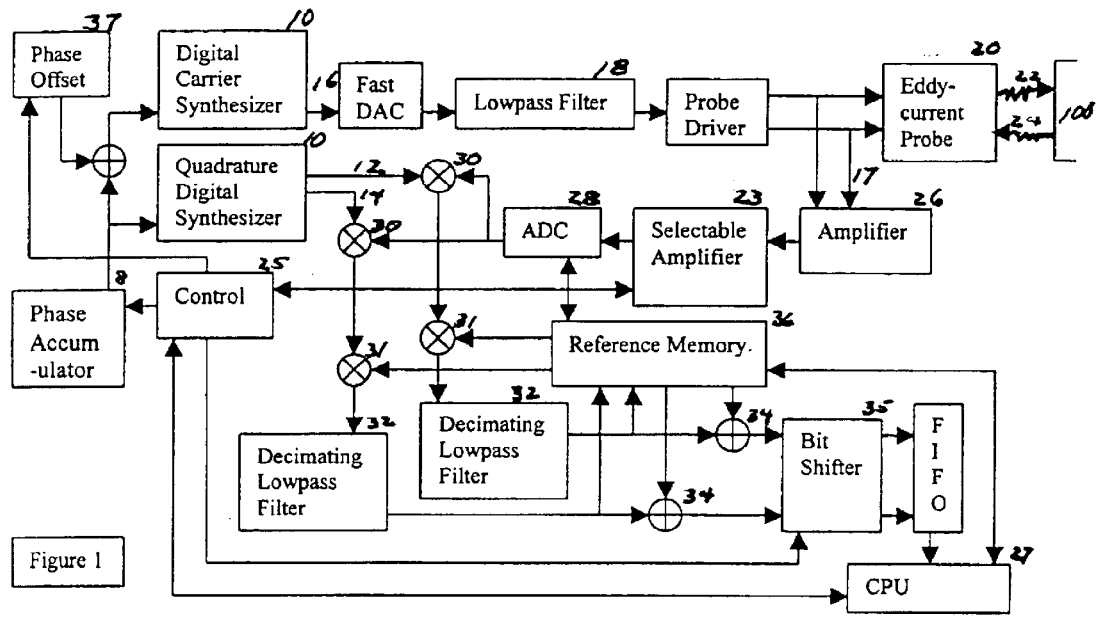
FIG. 1 is a block diagram of a circuit for digital signal processing of an eddy current signal.
Figure 2:
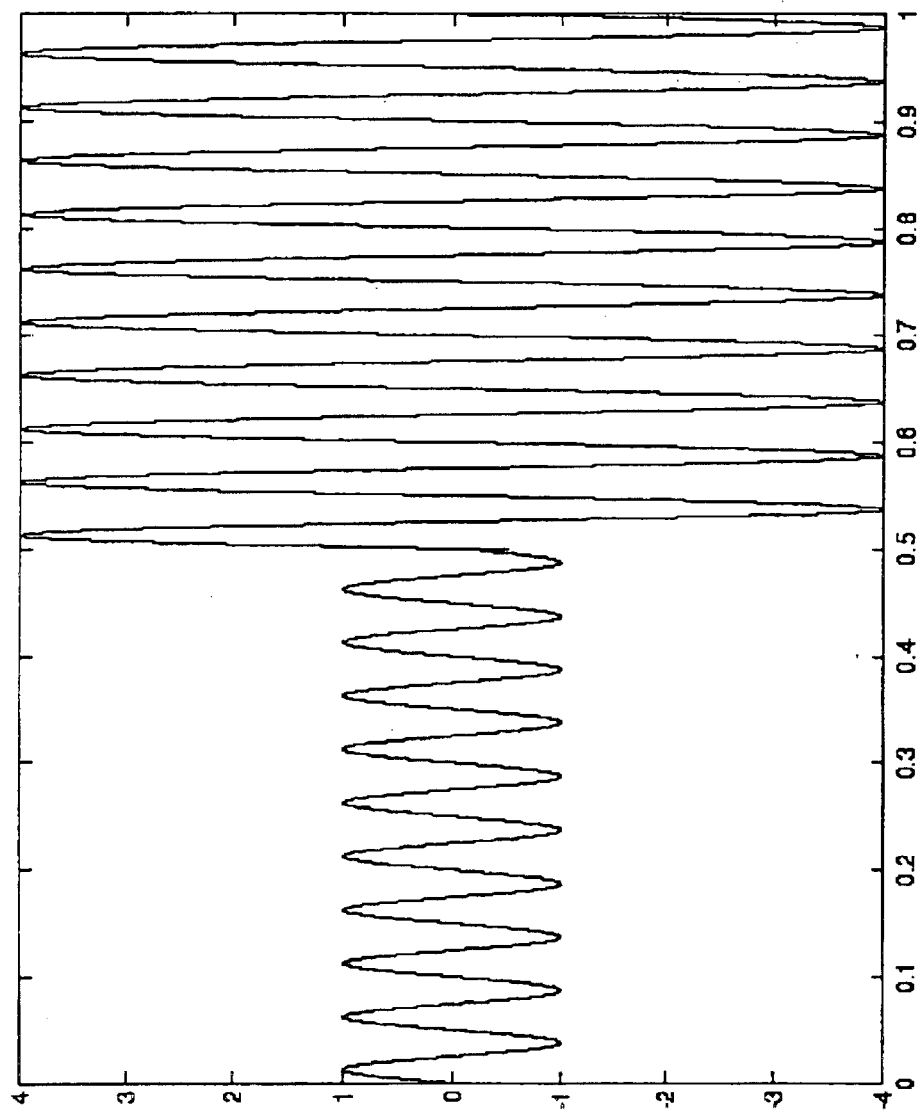
FIG. 2 is an example of selective amplification of a signal. Because the carrier signal was generated as a sine wave, and the carrier signal modulation due to return magnetic fields generated by eddy currents is small, the carrier signal continues to appear as a sinusoid. It is the nature of eddy current signal processing to remove this large carrier signal to reveal the remaining modulation on the carrier due to eddy currents. Eddy current probes are often employed in a differential circuit with two signal returns subtracted to remove much of the carrier signal. Where the differential amplifier is successful in removing a large portion of the carrier signal, this signal may be small. Otherwise, the signal will remain large. In some single-ended probe types a differential amplifier cannot be used, in which case the full carrier signal is amplified.
Figure 3:
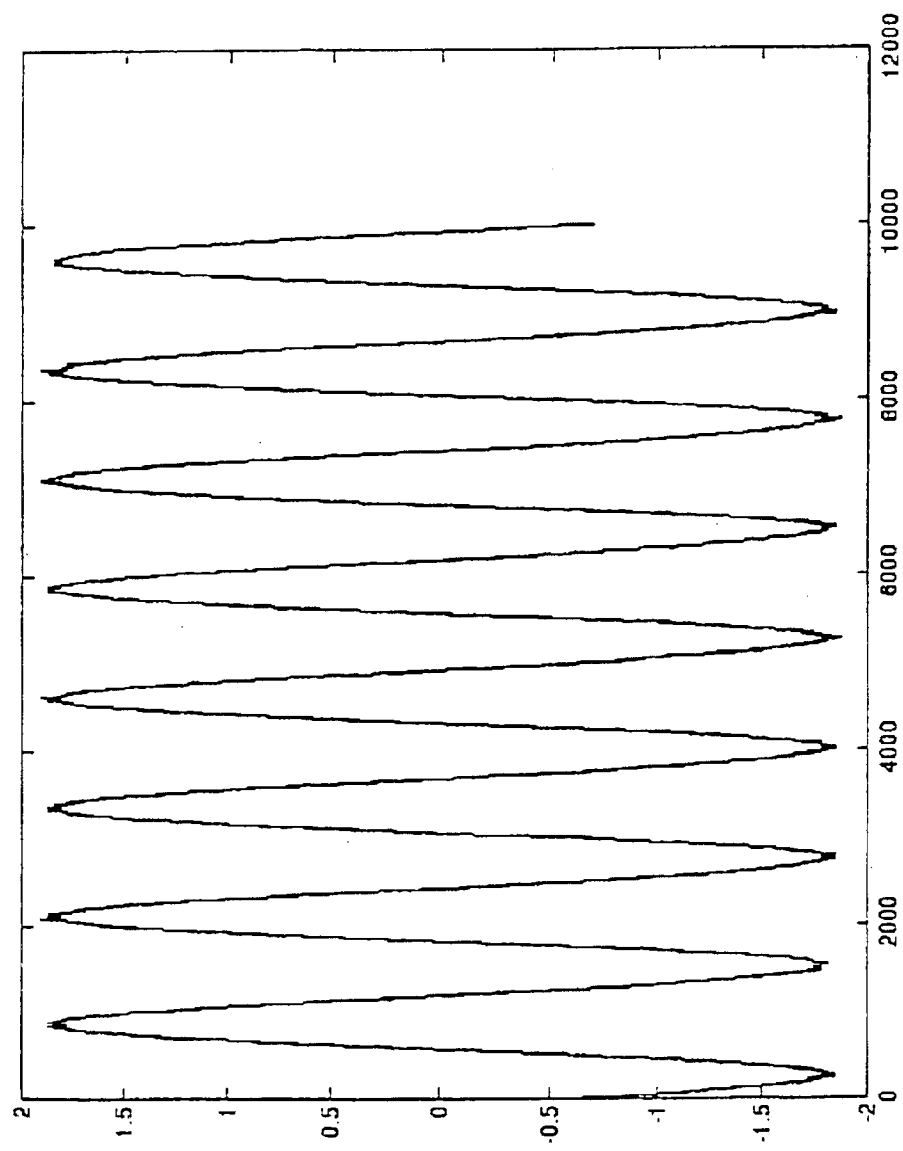
FIG. 3 illustrates a simple sinusoidal carrier with a relatively small and unnoticeable eddy current signal after amplification.
Figure 4:
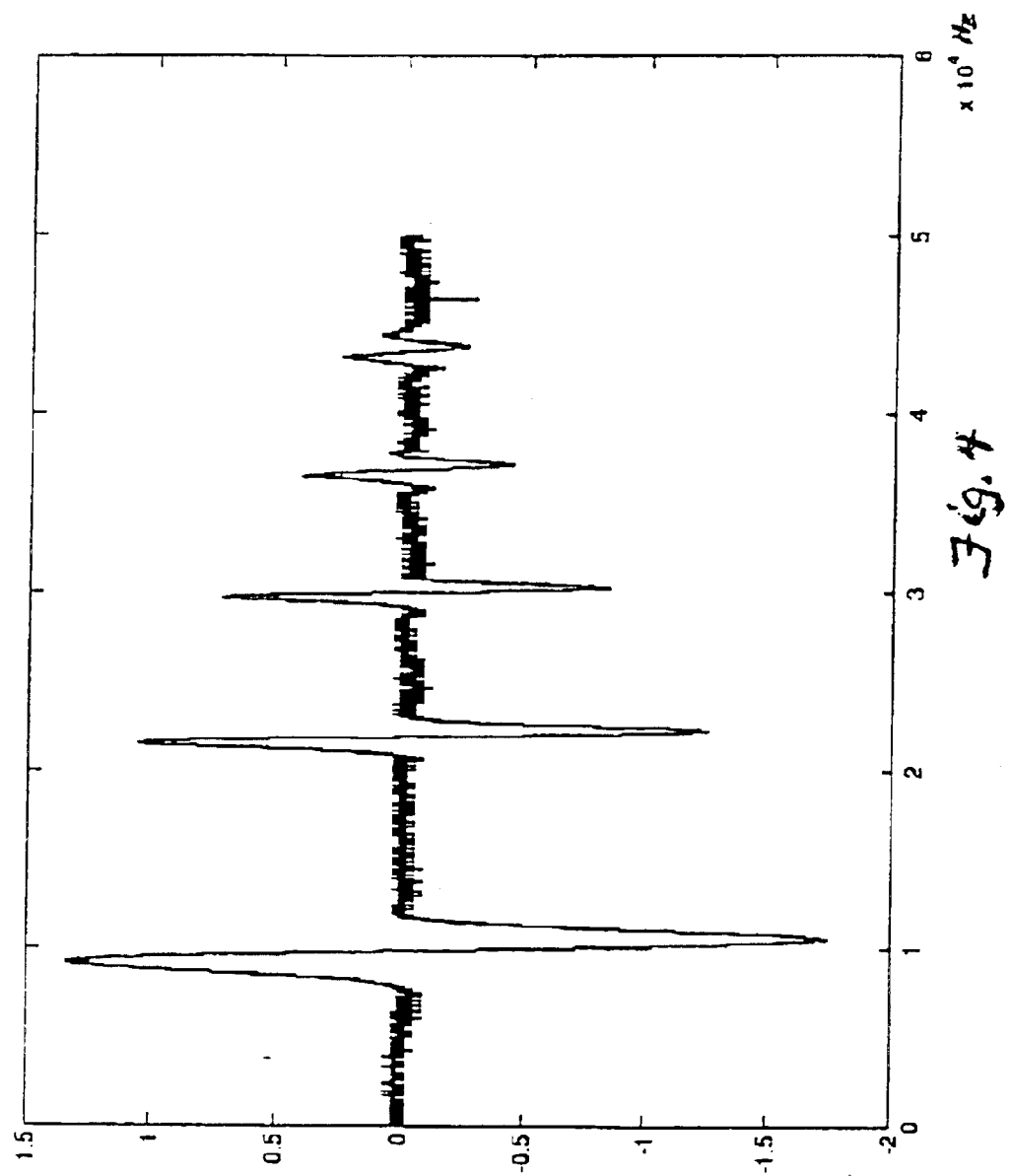
FIG. 4 and FIG. 5 are in-phase and quadrature components of an actual standard eddy current signal after it has been demodulated from the carrier signal of FIG. 3, derived by moving a probe through a tube that has some standard eddy current flaw signals.
Figure 5:
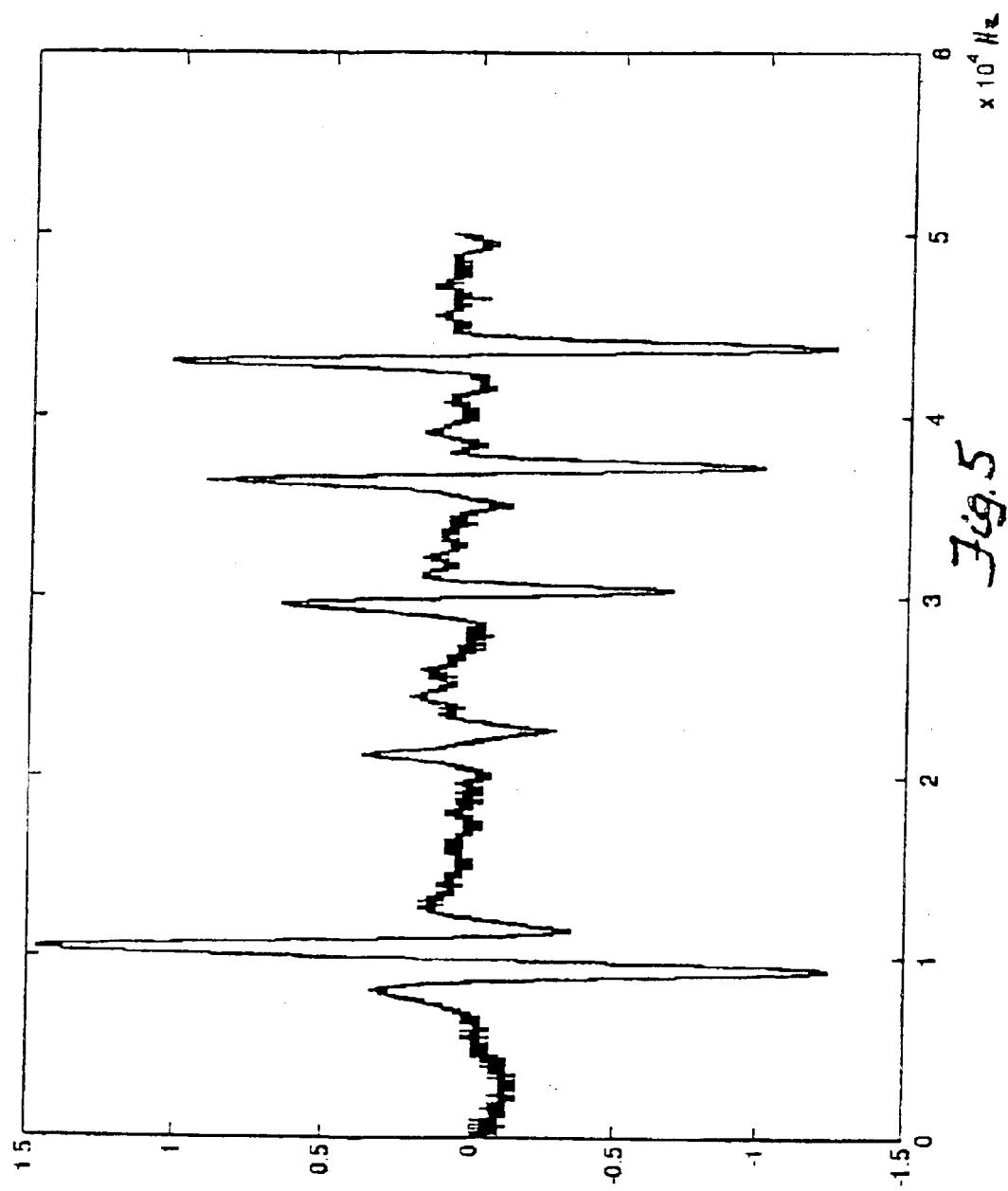

The present invention comprises a digital eddy current signal processing method and electronic circuit employing a dynamic gain control on signal amplification.

A phase accumulator 8 generates a linearly-increasing phase by iteratively adding an increment value to the current phase value. When the phase value exceeds the maximum value that can be expressed in the phase accumulator ($2^N-1$, where N is the number of bits in the phase accumulator), the overflow bit is simply discarded and the phase accumulator continues incrementing. The phase accumulator values represent a phase range from zero to 360 degrees. Larger increment values cause the phase accumulator to sweep through its range more frequently, thus generating higher frequencies. Therefore, the phase accumulator determines the frequency of synthesized carrier waves and sine and cosine waves.

A digital synthesizer 10 produces three digital sine waves 12, 14, and 16 from the phase output of the phase accumulator 8 that all have the same frequency, two of which are separated in phase by ninety degrees, establishing sine and cosine waves 12 and 14. The third wave 16 is the carrier sine wave, which has variable amplitude and phase relative to the sine and cosine waves.

The carrier signal 16 passes through a low-pass filter 18 and is driven to eddy current probe 20, which transmits an electromagnetic wave 22 into material 100 proximate the probe 20, generating eddy currents in the material. Defects in the material cause amplitude and phase differences in a return electromagnetic wave 24 generated by the eddy currents. The phase differences, or equivalently frequency changes, constitute a signature of the defects as a modulation of the return wave. The probe detects the return electromagnetic wave 24, now a modulated input carrier signal 17, through one or more probe coils. A first analog amplifier 26 amplifies the return signal from the probe. The first analog amplifier 26 typically includes an adjustable gain value that scales the return signal maximum amplitude to the input range of the analog-to-digital converter 28. A second analog amplifier 23, a selectable amplifier under computer control or user control, selectively scales the signal in sections to optimize the respective sections of the signal to the input range of the analog-to-digital converter 28.

After amplification, an analog-to-digital converter 28 digitizes the modulated input carrier signal 17, the digitizing rate determined by digital control logic. If the signal is digitized prior to amplification, the amplifier is also digital.

A digital mixer 30 demodulates the signal from the carrier signal 16. Digital sine and cosine waves 12 and 14 from the synthesizer 10 mathematically multiply digital input samples of the carrier signal 16 from the analog to digital converter 28 in the digital mixer 30. Multiplication by the sine and cosine waves creates in-phase and quadrature outputs useful for maintaining amplitude and phase information contained in the modulated input carrier signal 17 and a single-sideband complex translation of the real part of the modulated carrier wave 17. Unlike analog mixers, which also generate many unwanted mixer products, the digital mixer produces only sum and difference frequency signals without harmonics of the two signals.

A gain scaling stage 31 occurs after the demodulation stage as a fine adjustment to the gain introduced by the selectable filter to adjust for small differences between a desired amplification and the actual resulting amplification. In the scaling stage, each component of the eddy current signal is multiplied by a gain-scaling value. The gain-scaling value is equal to the desired gain ratio (a power of two) of the selectable amplifier divided by the actual (observed) gain ratio. In mathematical terms, the gain-scaling value is $$G_C = \frac{G_H \cdot G'_L}{G_L \cdot G'_H}$$

where $G_H/G_L$ is the desired gain ratio of the selectable amplifier, and $G'_L/G'_H$ is the ratio of the actual low gain of the selectable amplifier 23 to its actual high gain at the frequency of the phase accumulator. The actual gain ratio is calculated via a calibration procedure. The value $G_C$ is applied to the scaling multipliers in the gain scaling stage 31 when the high gain setting is selected in the selectable amplifier. The value 1.0 is applied to the scaling multipliers when the low gain setting is selected. For each treated signal section, both values are stored in reference memory 36.

To correct for phase changes of the selectable amplifier, controller 25 directs a phase offset 37 to adjust phase from the phase accumulator 8 before it outputs to the digital carrier synthesizer. The controller 25 examines the size of the digital signal from the analog to digital converter to determine and set the gain of the selectable amplifier. If the controller chooses a low gain (because the signal is large), then it also sets the phase offset 37 to zero degrees and the gain scaling value to 1.0. If the controller chooses a high gain for the selectable amplifier (because the signal is small), then it sets the phase offset 37 to be equal and opposite the phase change of the selectable amplifier, and it sets the gain scaling value to $G_C$. The controller also directs the bit shifter 35 to right-shift the quadrature eddy current signals when it chooses the high gain of the selectable amplifier. A computer 27 calculates the values of the phase offset and the gain scaling in a calibration procedure, which is an algorithm that is programmed into the computer.

While executing the calibration procedure, the computer 27 recognizes amplitude and phase discontinuities after the bit shifter and dictates adjustments in the gain scaling value and the phase offset value. The computer 27 communicates the adjusted values to the controller, which communicates them to the gain scaling stage 31, and to the phase offset stage 37. Then the controller sets the selectable amplifier 23 and bit shifters 35 accordingly in order to remove amplitude and phase discontinuities.

Decimating low-pass filters 32 then reject all but the difference frequencies, which together comprise the eddy current signal, effectively translating frequencies in the input signal to lower frequencies. With higher frequencies no longer present, the signal can be represented by a much smaller data sample in keeping with the Nyquist sampling theorem (any signal can be represented by discrete samples if the sampling rate is at least twice the bandwidth of the signal).

Following the decimating low-pass filters 32 is a digital direct current null circuit 34. To conveniently center the eddy current signal at zero so that it appears at the center of a display, the direct current value of the eddy current signal, which is stored in a reference memory 36, is subtracted from all signals that follow. The direct current reference signal is one of the outputs of the decimating low-pass filters 32. The reference memory 36 is queried for the direct current reference signal, which is then output and summed (subtracted) from the signal from the decimating low-pass filters. With the eddy current signal thus demodulated from the carrier wave 16 and centered about zero, it is available for display and analysis.

The bit shifter 35 reverses the sectional amplitude gain of the selectable amplifier 23 by shifting the bits in the signal words to the right to correspond with the gain applied by the selectable amplifier 23. Because each bit shift amounts precisely to a division by two the resultant signature will not be an exact reversal of the gain of selectable amplifier 23 although might be set to amplify the signal from the first amplifier by a power of two. Any real amplifier will not have a gain exactly equal to a power of two across the required frequency range (10 Hz to 10 MHz). This happens due to circuit performance shortcomings, such as electronic component drift from age or temperature, the variation of resistor values and the parasitic capacitances that exist on circuit boards. Therefore, a fine-tuning digital gain stage 31 is introduced after the multipliers 30 to trim the gain of the signal so the combination of the selectable amplifier and the digital gain stage results in an overall gain exactly equal to a power of two. Then the bit shifter 35 divides by the same power of two after the filters. Therefore, the combination of the selective amplification and the bit shifting is transparent to later signal analysis.

What is claimed is:

1. A method of amplifying an analog signal as it is being converted to a digital signal so as to exploit the range of an analog-to-digital converter throughout the signal through dynamic gain control, comprising the following steps:
   a. First, amplifying the signal;
   b. Second, selectively amplifying segments of the signal;
   c. Digitizing said signal;
   d. Adjusting amplification achieved in selectively amplifying segments of the carrier signal in a gain scaling stage such that resulting amplification of said signal segments is a power of two;
   e. Analyzing said amplified signal;
   f. Reversing said selective amplification of said signal segments selectively amplified by shifting bits in a digital representation of the signal.

2. A method of extracting a small signal modulated on an analog carrier signal in a digital circuit, comprising the following steps:
   a. In an electrical circuit, synthesizing digital sine and cosine functions;
   b. Amplifying the analog carrier signal to a maximum amplitude of an input range of an analog-to-digital converter;
   c. Selectively amplifying segments of the analog carrier signal by employing a amplifier under control of a computer that selectively scales the signal in sections by optimizing respective sections of the signal to the input range of the analog-to-digital converter;
   d. Digitizing said analog carrier signal into a digital carrier signal with the analog to digital converter;
   e. Mixing said digital carrier signal with said digital sinusoidal functions into quadrature components;
   f. Adjusting amplification achieved in selectively amplifying segments of the carrier signal in a gain scaling stage such that a resulting amplification of said signal segments is a power of two, a controller directing gain adjustment after examining the size of a digital signal from the analog to digital converter in order to set the gain of the amplifier, and wherein the controller sets the gain scaling value to $$G_C = \frac{G_H \cdot G'_L}{G_L \cdot G'_H}$$

where $G_H/G_L$ is a desired gain ratio of a selectable amplifier, and $G'_L/G'_H$ is the ratio of the actual low gain of the amplifier to its actual high gain at a frequency of a phase accumulator;
   g. Isolating the small signal by filtering said mixed digital carrier signal with a low-pass filter;
   h. Reversing said amplification of said signal segments selectively amplified by the controller setting the amplifier and a bit shifter to remove amplitude and phase discontinuities, the bit shifter shifting bits in a digital representation of the carrier signal, a computer calculating values of a phase offset and the gain scaling in a calibration algorithm programmed into the computer, said algorithm recognizing amplitude and phase discontinuities after the bit shifter and dictating adjustments in the gain scaling value and the phase offset value, the computer communicating the adjustments to the controller, which communicates them to the gain scaling and phase offset stage.

3. The method of claim 2 further including the step of adjusting a phase of the digital carrier signal before it is converted to analog correcting for unwanted phase changes to the carrier signal that occur in the amplifier by a controller directing introduction of a phase offset, if the controller chooses a low gain because the signal is large, then including the step of the controller also setting the phase offset to zero degrees and the gain scaling value to 1.0, but if the controller sets a high gain for the amplifier because the signal is small, then including the step of the controller also setting the phase offset to be equal and opposite the phase change of the amplifier.

* * * * *